(12) United States Patent
Accisano, III

(10) Patent No.: US 8,579,805 B2
(45) Date of Patent: Nov. 12, 2013

(54) MICROCATHETER TIP

(75) Inventor: Nicholas Gerald Accisano, III, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 1352 days.

(21) Appl. No.: 11/348,022

(22) Filed: Feb. 6, 2006

(65) Prior Publication Data

US 2007/0185446 A1 Aug. 9, 2007

(51) Int. Cl.
*A61B 1/00* (2006.01)

(52) U.S. Cl.
USPC .................................................. 600/184

(58) Field of Classification Search
USPC ............ 606/108; 604/104, 164.1, 524, 264, 604/164.11, 164.01; 600/184
See application file for complete search history.

(56) References Cited

U.S. PATENT DOCUMENTS

| | | | | |
|---|---|---|---|---|
| 3,406,685 A * | 10/1968 | May | ....................... | 604/164.11 |
| 4,698,056 A * | 10/1987 | Ciannella | ................ | 604/164.02 |
| 4,840,622 A * | 6/1989 | Hardy | ........................... | 604/264 |
| 5,205,830 A * | 4/1993 | Dassa et al. | ............... | 604/164.1 |
| 6,053,904 A * | 4/2000 | Scribner et al. | ............. | 604/527 |
| 6,368,301 B1* | 4/2002 | Hamilton et al. | ............ | 604/103 |
| 6,607,511 B2* | 8/2003 | Halseth et al. | ........... | 604/164.08 |
| 2002/0072712 A1* | 6/2002 | Nool et al. | ............... | 604/167.01 |
| 2005/0004523 A1* | 1/2005 | Osborne et al. | .......... | 604/164.01 |
| 2006/0135973 A1* | 6/2006 | Hawkins et al. | .............. | 606/167 |

* cited by examiner

*Primary Examiner* — Gary Jackson
*Assistant Examiner* — Jonathan Hollm
(74) *Attorney, Agent, or Firm* — Stoel Rives LLP

(57) ABSTRACT

The present invention is directed to a dilator having a stiffened shaft for use as part of an introducer sheath assembly. The dilator includes a stiffener tube and a tip of the dilator which extends distally to the dilator stiffener tube. The transition between the stiffener tube and the tip of the dilator is positioned such that when the dilator is positioned within the catheter sheath, the transition is also positioned within the catheter sheath. By positioning the transition between the stiffener tube of the dilator and the tip of the dilator inside the catheter sheath, the catheter sheath can provide strain relief subsequent to lateral movement of the tip of the dilator in a manner that can prevent kinking of the dilator tip at the transition between the stiffener tip and the tip of the dilator.

16 Claims, 6 Drawing Sheets

MICROCATHETER TIP

BACKGROUND OF THE INVENTION

1. The Field of the Invention

The present invention relates to catheters. In more particular, the present invention relates to an introducer sheath assembly having a reinforced dilator which minimizes kinking or bending of the dilator shaft.

2. The Relevant Technology

Catheters play an important role in the treatment and care of patients in modern medicine. In particular, catheters provide relatively unobtrusive access to remote portions of a patient's body, allowing desired procedures or treatments to be performed. A wide variety of generalized and specialized catheters have been developed and refined for particular uses. For example, angioplasty catheters have been adapted to provide a safe and effective conduit for the delivery of a stent and/or balloon to a narrowing or blockage in a patient's artery or vein. Typically, catheters are placed in a desired position within a patient utilizing a guidewire. The guidewire is threaded to the desired position within the patient and then the catheter is threaded over the guidewire.

One problem associated with some guidewires is that they have a diameter or thickness which requires a relatively large access puncture into the vasculature of the patient. The relatively large access puncture can result in damage to the artery or other patient tissue. Such damage can prolong the healing and/or bleeding time through the guidewire access point. Micropuncture catheters have been developed to provide a relatively smaller access puncture into the vasculature of the patient. Micropuncture introducer sheath assemblies include an introducer sheath which allows larger diameter guidewires to be introduced into the vasculature of the patient through the smaller access opening.

Utilizing a micropuncture introducer sheath assembly typically involves providing a small bore access puncture utilizing a small gauge needle. The needle is utilized to create an initial access puncture into the patient's vasculature. A small diameter guidewire is then threaded through the original puncture needle which has a smaller diameter than the guidewire which is to be utilized to guide the catheter to the desired location within the patient's vasculature. In one example, a guidewire having an 0.018" diameter is utilized.

Once the micropuncture guidewire is positioned within the patient's vasculature, the original access needle can be withdrawn from the patient. An introducer sheath assembly is then threaded over the micropuncture guidewire. Typically, the catheter sheath has a somewhat resilient configuration which allows for desired operability in subsequent steps of the procedure. The dilator is positioned within the catheter sheath to provide additional rigidity required to insert the catheter sheath into the patient. Additionally, the dilator's tapered tip transitions from the guidewire's outer diameter to the diameter at the distal end of the sheath. The dilator typically includes a resilient dilator shaft which is sufficiently stiff to allow for access into the patient along the guidewire, but sufficiently resilient to prevent unneeded damage to the patient. Once the introducer sheath assembly has been introduced into the patient, the guidewire is withdrawn from the patient and subsequently the dilator is also withdrawn from the patient leaving the catheter sheath in place. A subsequent and larger diameter guidewire can then be introduced through the introducer sheath without the need to create a larger access puncture in the vasculature of the patient. Once the larger diameter guidewire is inserted into the patient, the catheter sheath can be withdrawn and the guidewire can be manipulated as required for proper placement of the guidewire in the patient's vasculature or within another position within the patient's body.

One problem that has been encountered with the use of such introducer sheath assemblies relates to introducer sheath assemblies that include a stiffener tube as part of the dilator. The transition between the stiffening tube and the tip of the dilator sometimes buckles or kinks during the insertion of the introducer sheath assembly into the patient. This is typically due to the fact that the stiffening tube that is positioned within the dilator has a greater rigidity and strength than the material from which the tip of the dilator is formed. As a result, multiple introducer sheath assemblies may need to be utilized during a single insertion procedure to allow for completion of the procedure once an initial dilator tip has failed. This can increase the time needed to complete the procedure, as well as cost due to the fact that multiple micropuncture catheters are utilized during the course of the procedure. A number of different approaches have been developed to attempt to strengthen dilators and dilator tips, however, such attempts can often be overly costly or fail to provide the desired properties to compensate for failure of such dilator tips.

BRIEF SUMMARY OF THE INVENTION

The present invention is directed to a dilator having a stiffened shaft for use as part of an introducer sheath assembly. The dilator is typically utilized within a catheter sheath which is to be inserted into a patient. The catheter sheath typically comprises a somewhat resilient tubular member which can be difficult to insert into the patient. The dilator provides additional rigidity to allow for insertion of the catheter sheath into the vasculature or body cavity of a patient. The dilator can include a stiffener which extends from the proximal end of the dilator to the distal end of the dilator. A tip of the dilator extends distally to the dilator stiffener. The dilator tip has an increased degree of flexibility and/or resilience, which allows for insertion of the tip of the dilator into the patient in a manner that does not result in damage or unnecessary tearing of the patient's tissue.

According to one embodiment of the present invention, the transition between the stiffener and the tip of the dilator is positioned such that when the dilator is positioned within the catheter sheath, the transition is also positioned within the catheter sheath. In other words, a portion of the tip of the dilator is positioned inside the catheter sheath and a portion of the tip of the dilator is positioned outside the tip of the catheter sheath. By positioning the transition between the stiffener of the dilator and the tip of the dilator inside the catheter sheath, the catheter sheath can provide strain relief subsequent to lateral movement of the tip of the dilator in a manner that can reduce or prevent kinking of the dilator tip at the transition between the stiffener tip and the tip of the dilator. According to one embodiment of the present invention, the tip of the dilator is longer than traditional dilator tips allowing for positioning of the transition further back relative to the catheter sheath than known introducer sheath assemblies. In another embodiment, the catheter sheath is longer than traditional catheter sheaths such that the tip of the catheter sheath is positioned distally to the transition between the tip of the catheter and the catheter stiffener.

According to one embodiment of the present invention, the tip of the dilator is formed from a sleeve which is external to the stiffener tube and runs along the length of the stiffener tube. The sleeve extends an amount beyond the distal end of the stiffener providing a tip at the distal end of the dilator. According to one embodiment of the present invention, the tip of the dilator includes a flow back region which is in contact with the tip of the stiffener when a force is exerted against the end of the dilator tip. In this manner, contact surfaces are provided between the stiffener and the dilator tip providing additional strength to the tip portion of the sleeve in a manner that minimizes buckling of the sleeve.

According to one embodiment of the present invention, the dilator is manufactured by positioning the sleeve over the stiffener tube. A mandrel is positioned within the stiffener up to the distal end of the dilator, including the portion of the dilator corresponding with the tip portion of the sleeve. A die is also positioned along the length of the dilator adjacent the sleeve and/or the stiffener tube. A radio frequency or other heat source medium flows through the mandrel and die and is exerted on the sleeve and stiffener tube. Heating of the sleeve and stiffener tube forms the sleeve to the stiffening tube. Forming of the sleeve to the stiffening tube allows for proper operation of the dilator during the procedure for which the introducer sheath assembly is to be utilized.

During heating of the sleeve, the tip portion of the sleeve begins to flow back into the air gap region between the mandrel and the sleeve proximate the distal tip of the stiffener tube. This is largely due to the fact that the mandrel is configured to have an outside diameter which approximates the inside diameter of the stiffener tube. The sleeve is configured to slide over the outside diameter of the stiffener tube. As a result, an air gap is formed between the inside diameter of the sleeve and the smaller diameter of the mandrel in the tip portion of the dilator that extends beyond the stiffener tube. Once the sleeve has been sufficiently heated such that flow back has been achieved into the gap between the tip of the sleeve and the mandrel, a contact surface is provided on the tip of the sleeve against the forward facing surface of the stiffener tube. The mandrel and die can be removed subsequent to proper formation of the tip of the dilator.

According to one embodiment of the present invention, the dilator tip includes both a flow back portion or other contact surface to interface with the stiffener tube and a transition between the stiffener tube and the dilator tip which is positioned within the catheter sheath. By providing both a contact surface, a transition which can be positioned within the catheter sheath. Positioning of the transition in the catheter sheath provides a stronger, more reliable, and kink-resistant catheter tip.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
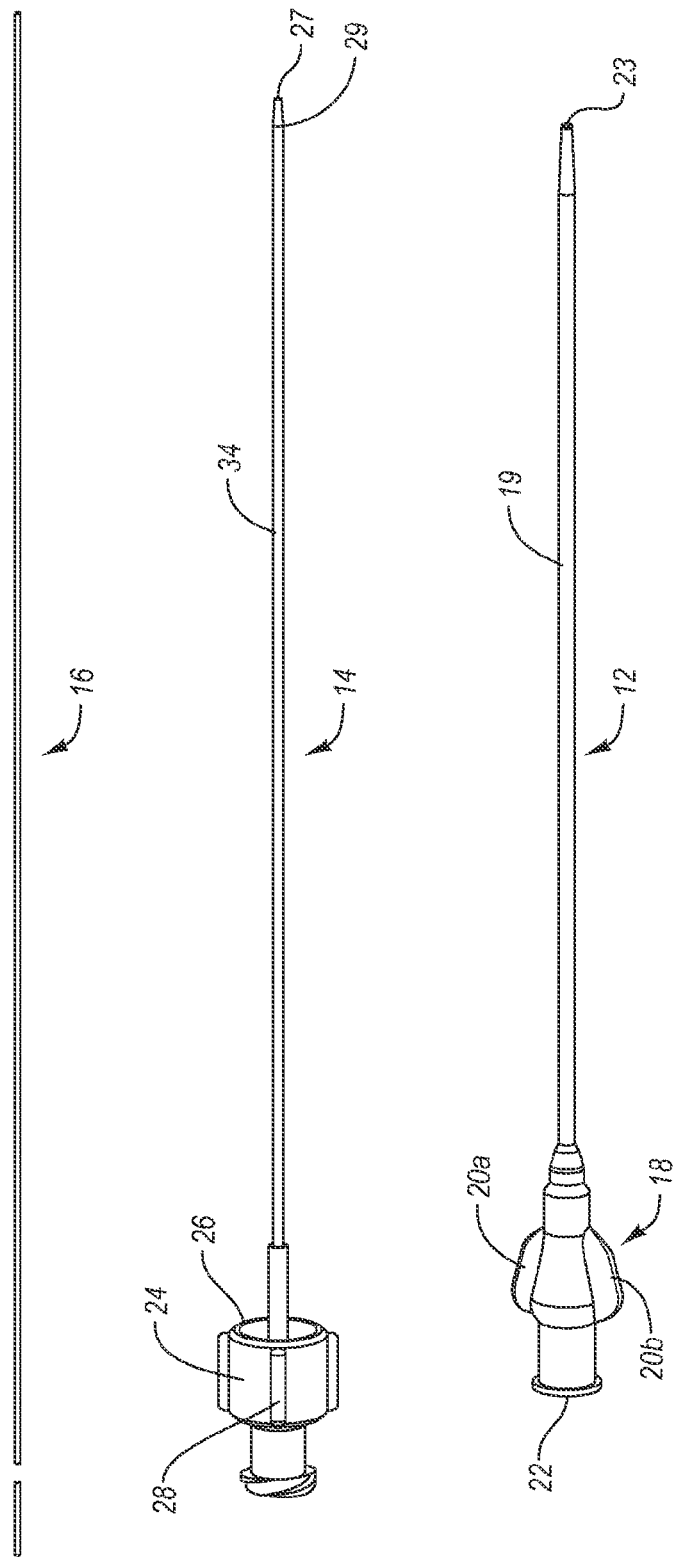
FIG. 1 is a perspective component view of an introducer sheath assembly, according to one embodiment of the present invention.

The present invention is directed to a dilator having a stiffened shaft for use as part of an introducer sheath assembly. The dilator is typically utilized within a catheter sheath which is to be inserted into a patient. The catheter sheath typically comprises a somewhat resilient tubular member which can be difficult to insert into the patient. The stiffened dilator provides additional rigidity to allow for insertion of the catheter sheath into the vasculature or body cavity of a patient. The stiffened dilator includes a stiffener which extends from the proximal end of the dilator shaft to the distal end of the dilator. A tip of the dilator extends distally to the stiffener tube. The dilator tip has an increased degree of flexibility and/or resilience, which allows for insertion of the tip of the dilator into the patient in a manner that does not result in damage or unnecessary tearing of the patient's tissue.

According to one embodiment of the present invention, the transition between the stiffener and the tip of the dilator is positioned such that when the dilator is positioned within the catheter sheath, the transition is also positioned within the catheter sheath. In other words, a portion of the tip of the dilator is positioned inside the catheter sheath and a portion of the tip of the dilator is positioned outside the tip of the catheter sheath. By positioning the transition between the stiffener tube of the dilator and the tip of the dilator inside the catheter sheath, the catheter sheath can provide strain relief subsequent to lateral movement of the tip of the dilator in a manner that can prevent kinking of the dilator tip at the transition between the stiffener tube and the tip of the dilator. According to one embodiment of the present invention, the tip of the dilator is longer than traditional dilator tips allowing for positioning of the transition further back relative to the catheter sheath than known introducer sheath assemblies. In another embodiment, the catheter sheath is longer than traditional catheter sheaths such that the tip of the catheter sheath is positioned distally to the transition between the tip of the catheter and the catheter stiffener.

According to one embodiment of the present invention, the tip of the dilator is formed from a sleeve which is external to the stiffener tube and runs along the length of the stiffener tube. The sleeve extends an amount beyond the distal end of the stiffener tube providing a tip at the distal end of the dilator. According to one embodiment of the present invention, the tip of the catheter includes a flow back region which is in contact with the tip of the stiffener tube when a force is exerted against the end of the dilator tip. In this manner, contact surfaces are provided between the stiffener tube and the dilator tip providing additional strength to the tip portion of the sleeve in a manner that minimizes buckling of the sleeve.

According to one embodiment of the present invention, the dilator is manufactured by positioning the sleeve over the stiffener tube. A mandrel is positioned within the length of the stiffener tube up. to the distal end of the dilator, including the portion of the dilator corresponding with the tip portion of the sleeve. A die is also positioned along the length of the dilator adjacent the sleeve and/or the stiffener tube. A radio frequency or other heat source medium flows through the mandrel and die and is exerted on the sleeve and stiffener tube. Heating of the sleeve and stiffener tube forms the sleeve to the dilator tube. Forming of the sleeve to the dilator allows for proper operation of the dilator during the procedure for which the introducer sheath assembly is to be utilized.

During heating of the sleeve, the tip portion of the sleeve begins to flow back into the air gap region between the mandrel and the sleeve proximate the distal tip of the stiffener tube. This is largely due to the fact that the mandrel is configured to have an outside diameter which approximates the inside diameter of the stiffener tube. The sleeve is configured to slide over the outside diameter of the stiffener tube. As a result, an air gap is formed between the inside diameter of the sleeve and the smaller diameter of the mandrel in the tip portion of the dilator that extends beyond the stiffener tube. Once the sleeve has been sufficiently heated such that flow back has been achieved into the gap between the tip of the sleeve and the mandrel, a contact surface is provided on the tip of the sleeve against the forward facing surface of the stiffener tube. The mandrel and die can be removed subsequent to proper formation of the tip of the dilator.

According to one embodiment of the present invention, the dilator tip includes both a flow back portion or other contact surface to interface with the stiffener tube and a transition between the stiffener tube and the dilator tip which is positioned within the catheter sheath. By providing both a contact surface, a transition which can be positioned within the catheter sheath. Positioning of the transition in the catheter sheath provides a stronger, more reliable, and kink-resistant dilator tip.

FIG. 1 is a perspective view of an introducer sheath assembly 10, according to one embodiment of the present invention. Introducer sheath assembly 10 is utilized to facilitate the introduction of a guidewire or catheter into the vasculature or other body cavity of a patient. Micropuncture catheters have been developed to provide a relatively smaller access puncture into the vasculature of the patient. Micropuncture introducer sheath assemblies include an introducer sheath which allows larger diameter guidewires to be introduced into the vasculature of the patient through the smaller access opening.

During a procedure, micropuncture introducer sheath assembly 10 is utilized to provide a small bore access puncture utilizing a small gauge needle (for example a 21 gauge needle). The needle is utilized to create an initial access puncture into the patient's vasculature. A small diameter guidewire is then threaded through the small gauge puncture needle. The small diameter guidewire has a smaller diameter than the guidewire which is to be utilized to guide the catheter to the desired location within the patient's vasculature. In one example, a guidewire having an 0.018" diameter is utilized.

Once the guidewire is positioned within the patient's vasculature, the original access needle can be withdrawn from the patient. An introducer sheath assembly is then threaded over the micropuncture guidewire. The introducer sheath assembly can include a stiffening dilator which is positioned inside a catheter sheath (also sometimes referred to as an introducer). Typically, the catheter sheath has a somewhat resilient configuration which allows for desired operability in subsequent steps of the procedure. The resilient nature of the catheter sheath can make it difficult to introduce the catheter sheath into the vasculature of the patient without a stiffening dilator. The dilator is positioned within the catheter sheath to provide additional rigidity required to insert the catheter sheath into the patient. A stiffened dilator typically includes a stiffening tube along the length of the dilator and a somewhat more resilient dilator tip which is sufficiently stiff to allow for access into the patient along the guidewire, but sufficiently resilient to prevent unneeded damage to the patient.

Once the introducer sheath assembly has been introduced into the patient, the guidewire is withdrawn from the patient and subsequently the dilator is also withdrawn from the patient leaving the catheter sheath in place. A subsequent and larger diameter guidewire can then be introduced through the introducer sheath without the need to create a larger access puncture in the vasculature of the patient. Once the larger diameter guidewire is inserted into the patient, the catheter sheath can be withdrawn and the guidewire can be manipulated as required for proper placement of the guidewire in the patient's vasculature or within another position within the patient's body.

In the illustrated embodiment, introducer sheath assembly 10 comprises a catheter sheath 12, a dilator 14, and a guidewire 16. During a procedure in which introducer sheath assembly 10 is utilized, catheter sheath 12 and dilator 14 will typically be coupled together allowing the introducer sheath assembly 10 to be threaded into the patient. Dilator 14 is inserted along the length of catheter sheath 12 to provide rigidity and stiffness to facilitate the insertion of catheter sheath 12 into the patient. To insert catheter sheath 12 and dilator 14 into the patient, guidewire 16 is first inserted into the desired position within the patient through an access needle which has been inserted through the skin of the patient and into a vein, artery, or body cavity. Once guidewire 16 has been threaded through the access needle and into the patient, the needle can be withdrawn leaving guidewire 16 in place within the patient.

The relatively small diameter of the components of a micropuncture introducer sheath assembly 10 allow for a relatively small access puncture into the patient. For example, typically the access needle utilized with guidewire 16 can be a 21 gauge access needle or smaller. This allows a smaller guidewire 16 to be utilized. For example, guidewire 16 can be a 0.018" guidewire or smaller. By utilizing such small access needles and guidewires with introducer sheath assembly 10, the original access puncture to the patient's skin, body cavity, or vasculature is quite small. The small access puncture facilitates a shorter recovery time, less trauma to the patient, and while abbreviating the length of bleeding from the access puncture and/or the vasculature of the patient.

Once guidewire 16 is positioned in the desired location within the patient, dilator 14 is threaded over guidewire 16. As previously discussed, dilator 14 is positioned within catheter sheath 12 such that when guidewire 16 is threaded along the length of dilator 14, guidewire 16 is also threaded along the length of catheter sheath 12. Dilator 14 and catheter sheath 12 are then advanced along the length of guidewire 16 through the access puncture in the patient's skin and into the desired position within the patient's body. The configuration of the tip of catheter sheath 12 and dilator 14 result in little tearing or trauma at the access puncture. Instead, catheter sheath 12 and dilator 14 results in stretching of the access puncture in a manner such that the size of the access puncture quickly returns to the original puncture size allowing for quicker healing at the, access puncture site. Once dilator 14 and catheter sheath 12 have been inserted into the patient, guidewire 16 is withdrawn from the patient. Subsequently, dilator 14 will be withdrawn from the catheter sheath 12 allowing for the practitioner to access the body cavity or vasculature of the patient through catheter sheath 12.

In one embodiment, a larger diameter guidewire can be threaded through catheter sheath 12 and into the vasculature of the patient without requiring a larger access puncture typically required when a larger guidewire is inserted directly through an access needle. For example, such larger diameter guidewires can be a 0.038" diameter guidewire which requires an approximately 0.040" diameter puncture needle to be inserted into the patient. Utilizing a 0.040" diameter-puncture needle instead of the exemplary 21 gauge needle which is utilized in connection with catheter sheath 12 results in an access puncture that can be more that twice the size of the puncture required when utilizing introducer sheath assembly 10.

In the illustrated embodiment, catheter sheath 12 comprises a sheath hub 18 and a sheath tube 19. Sheath tube 19 is coupled to sheath hub 18 in a manner that allows for desired operation of sheath tube 19 relative to sheath hub 18. Additionally, sheath tube 19 is in fluid communication with sheath hub 18 allowing access to sheath tube 19 along the length of sheath hub 18.

In the illustrated embodiment, sheath hub 18 comprises wings 20a, b and a lower coupler 22. Wings 20a, b facilitates manipulation of catheter sheath 12 and introducer sheath assembly 10 by providing a gripping point for the practitioner during utilization of the introducer sheath assembly 10. Lower coupler 22 is positioned at the proximal end of catheter sheath 12. Lower coupler 22 allows for coupling of the dilator 14 to the catheter sheath 12 during operation of the introducer sheath assembly.

Sheath tube 19 includes a sheath tip 23 positioned at the distal end of the sheath tube 19. Sheath tip 23 is slightly tapered allowing for insertion of the catheter sheath into the access puncture. Sheath tube 19 typically has a resilient and somewhat flexible configuration allowing for introduction of larger diameter guidewires along the length of catheter sheath 12. The resilient nature of sheath tube 19 also permits expansion of the access puncture in the patient's skin while protecting the patient from damage as the guidewire is inserted.

Dilator 14 comprises a dilator hub 24 and a stiffener tube 32. Stiffener tube 32 provides additional rigidity and strength to dilator sleeve 34 as introducer sheath assembly 10 is inserted into the patient. Dilator hub 24 allows for manipulation of stiffener tube 32 while also allowing for coupling of the dilator 14 to the catheter sheath 12 during utilization of the introducer sheath assembly 10. In the illustrated embodiment, dilator hub 24 comprises a lower coupler 26 and gripping members 28. Lower coupler 26 is positioned on the distal side of dilator hub 24 allowing for mating engagement of dilator hub 24 and sheath hub 18. Gripping members 28 are positioned on the outside diameter of dilator hub 24 allowing for gripping of the dilator hub 24 by the practitioner. By gripping the dilator hub 24, the practitioner can manipulate the dilator 14 to secure the dilator hub 24 to the sheath hub 18. Additionally, gripping members 28 of dilator hub 24 allow the practitioner to manipulate the introducer sheath assembly 10 during the course of the procedure.

Dilator sleeve 34 includes a dilator tip 27. Dilator tip 27 comprises a somewhat resilient member which is configured to prevent damage to the patient tissue as introducer sheath assembly 10 is threaded along the length of guidewire 16 and into the patient. Dilator tip 27 is somewhat more resilient and deformable than stiffener tube 32. This is due to the fact that the stiffener tube is positioned within dilator sleeve 34 but does not extend into dilator tip 27.

Transition 29 represents the point at which the stiffener tube terminates and dilator tip 27 begins. In the illustrated embodiment, transition 29 is positioned at a point that is more proximal than traditional transition points on stiffened micropuncture catheters. This allows for transition 29 to be positioned proximally to the sheath tip 23 of catheter sheath 12 when dilator 14 is threaded along the length of catheter sheath 12 and dilator hub 24 is coupled to sheath hub 18. Additionally, dilator tip 27 has a greater length from transition 29 to the distal tip of dilator tip 27. The greater length of dilator tip 27 allows a portion of dilator tip 27 to be positioned proximally to sheath tip 23 and within the catheter sheath 12. Additionally, a portion of dilator tip 27 can be positioned outside of catheter sheath 12 and distally to sheath tip 23.

The positioning of transition 29 within catheter sheath 12 allows catheter sheath 12 to provide strain relief to dilator tip 27 subsequent to lateral movement of the dilator tip 27. Positioning transition 29 within catheter sheath 12 relieves the strain that would normally be carried primarily at transition 29. Such strain is caused due to the stiffer configuration of dilator sleeve 34, which is co-extensive with the stiffener tube 32, and the more flexible nature of dilator tip 27. By providing strain relief subsequent to lateral movement of dilator tip 27, potentially damaging forces at transition 29 are dissipated. By dissipating such forces, kinking, buckling, or bending of catheter tip 27 at transition 29 is minimized in a manner that could result in the failure of dilator tip 27 during the procedure. In other words, minimizing the potential for damage at transition 29 provides for continued integrity of dilator 14 during the course of an insertion procedure.

As will be appreciated by those skilled in the art, a variety of types and configurations of introducer sheath assemblies can be utilized without departing from the scope or spirit of the present invention. For example, in one embodiment, the transition point is positioned at a traditional location along the length of the dilator. An elongate catheter sheath is provided such that the sheath tip is positioned distally to the transition. In another embodiment, a standard sized catheter sheath is utilized with a dilator having a shorter stiffener. An elongated dilator tip is provided such that the transition is moved proximally behind the tip of the catheter sheath. In yet another embodiment, a combination of an elongated catheter sheath, an elongated dilator tip, and a proximally positioned transition is utilized to provide a strengthened dilator tip. In yet another embodiment, the dilator hub is secured to the sheath hub utilizing other than a lower coupling. In yet another embodiment, a single hub is provided instead of two hubs.

Figure 2:
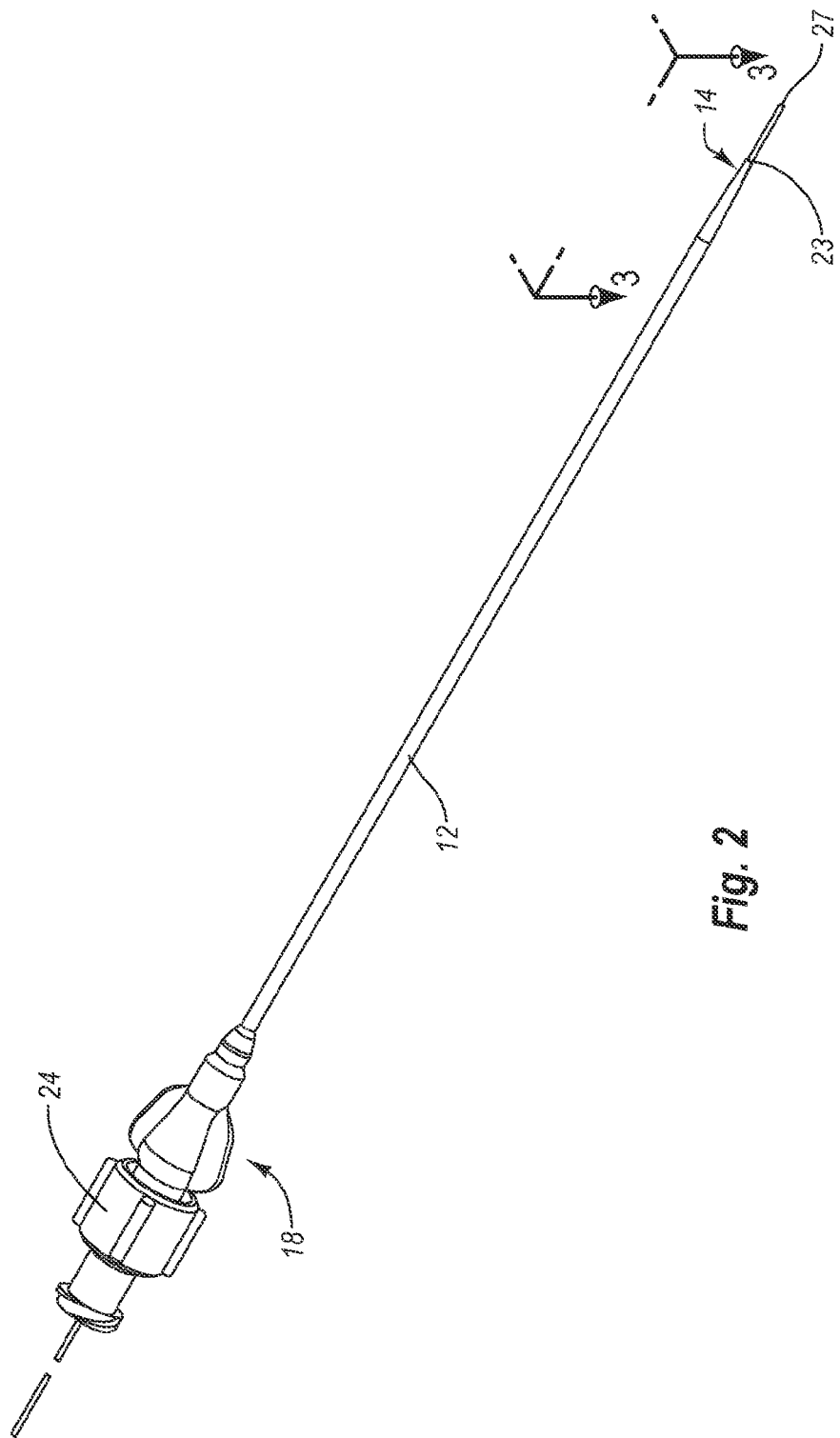
FIG. 2 is a perspective view of an introducer sheath assembly which has been assembled for use in a procedure.
Figure 3:
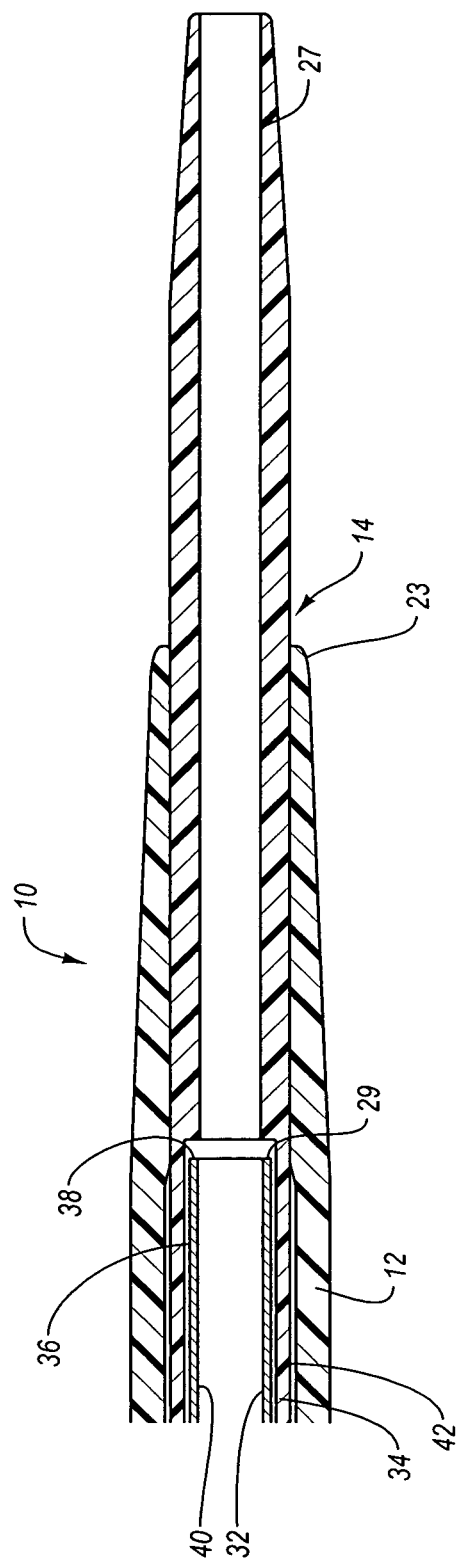
FIG. 3 is a close-up cross-sectional view of the tip of the introducer sheath assembly illustrating the juxtaposition of the stiffener tube, transition, sleeve, and catheter sheath, according to one embodiment of the present invention.

With reference now to FIGS. 2 and 3, FIG. 2 is a perspective view of an introducer sheath assembly according to one embodiment of the present invention. In the illustrated embodiment, dilator 14 is threaded along the length of catheter sheath 12. Dilator hub 24 is secured to sheath hub 18 such that catheter sheath 12 and dilator 14 operate as a single insertion instrument in cooperation with a guidewire 16 (see FIG. 2). As previously discussed, a practitioner grasps one or both of sheath hub 18 and dilator hub 24 to guide dilator tip 27 over the guidewire 16 and into the insertion point as desired during the procedure.

In the illustrated embodiment, a cross-sectional view is taken along lines 3-3 of FIG. 2 and is depicted in FIG. 3. FIG. 3 illustrates the juxtaposition of sheath tip 23 relative to dilator tip 27 at transition 29. Transition 29 is positioned proximally to sheath tip 23 such that transition 29 is positioned within catheter sheath 12. Dilator tip 27 extends from transition 29 to the distal end of dilator 14.

Dilator tip 27 has an elongated configuration such that a portion of dilator tip 27 is positioned inside catheter sheath 12 and a portion of dilator tip 27 is positioned outside of catheter sheath 12 and proximally to sheath tip 23. As dilator tip 27 contacts the patient's skin or other patient tissue, a force is exerted against dilator tip 27. The force exerted against dilator tip 27 can result in lateral movement and/or lateral pressure on dilator tip 27. Such lateral movement and lateral pressure is typically conveyed along the length of the distal end of dilator 14 in a manner that can result in strain at transition 29.

The configuration of the stiffener tube 32 and dilator tip 27 results in strain at transition 29. As a result, transition 29 can be a common point of failure, such as buckling or kinking of dilator tip 27, during the insertion of the introducer sheath assembly into the patient. Catheter sheath 12 is configured such that interior walls of the sheath tip 23 contact the exterior walls of dilator tip 27. During lateral movement of dilator tip 27, contact between dilator tip 27 and sheath tip 23 allows sheath tip 23 to provide strain relief along part, or all, of the length of dilator tip 27. By providing strain relief along the length of dilator tip 27, sheath tip 23 minimizes the pressure or torsion experienced at transition 29 in a manner which can substantially reduce the likelihood of failure at transition 29.

In the illustrated embodiment, dilator 14 comprises a stiffener tube 32 and a sleeve 34. Stiffener tube 32 provides rigidity and strength to dilator 14 that allows dilator 14 to facilitate introduction of catheter sheath 12 into the patient. In the illustrated embodiment, stiffener tube 32 comprises a flexible metal, hard plastic, or other material which provides sufficient rigidity and strength to maintain the configuration of dilator 14. Sleeve 34 is positioned externally to stiffener tube 32. Sleeve 34 provides an outer coating to stiffener tube 32 that facilitates sliding of dilator 14 along the length of catheter sheath 12 during insertion of dilator 14 into catheter sheath 12. Additionally, sleeve 34 comprises the material from which dilator tip 27 is formed. The configuration of sleeve 34 allows for quick and efficient manufacturing of dilator 14. For example, the configuration of sleeve 34 allows for automation of the manufacturing process in a manner that substantially minimizes the cost of manufacturing the dilator 14.

In the illustrated embodiment, a dilator inside diameter 40 is determined by the inside diameter of stiffener tube 32. The dilator outside diameter 42 is determined by the outside diameter of the sleeve 34. Sleeve 34 is coupled to stiffener tube 32 at the stiffener tube/sleeve interface 36. In one embodiment of the present invention, sleeve 34 is ultrasonically welded to stiffener tube 32 at the stiffener tube/sleeve interface 36. In another embodiment, the sleeve is formed to the stiffener tube/sleeve interface utilizing a heat source medium, adhesive, or other known chemical or mechanical forming processes.

As will be appreciated by those skilled in the art, a variety of types and configurations of dilators can be utilized without departing from the scope and spirit of the present invention. According to one embodiment of the present invention, a stiffened support member, or ring, is provided within the introducer sheath located at the juncture of the stiffener tube and dilator tip, further reinforcing the joint. According to another embodiment, a solid support member is provided. According to another embodiment, a braided, woven, wrapped or other support member. According to another embodiment, a support member is formed having a co-extrusion or a portion having a co-extrusion. According to yet another embodiment, a support member is located within the dilator.

Figure 4:
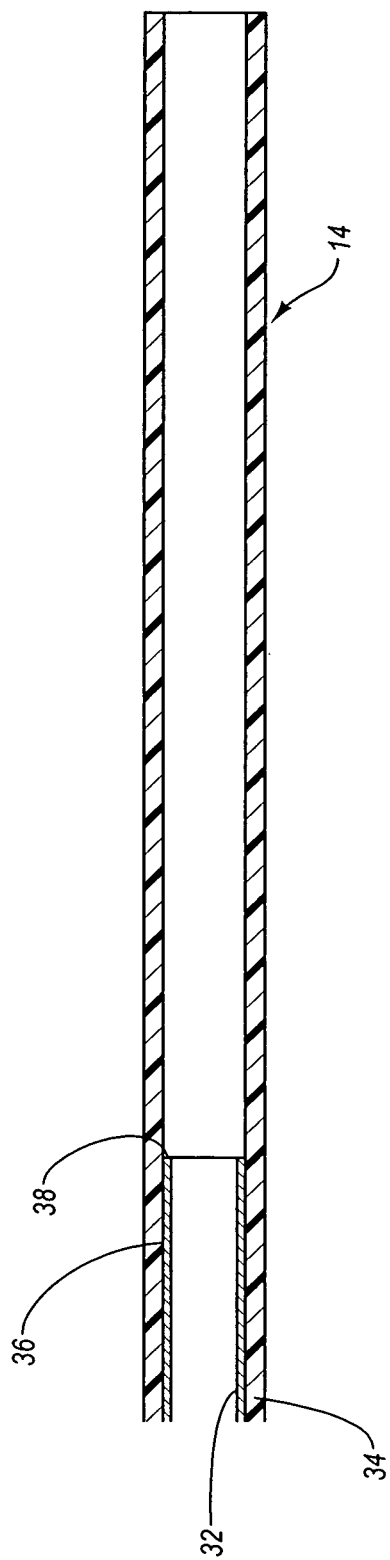
FIG. 4 is a perspective view of an introducer sheath assembly illustrating the positioning-of the sleeve relative to the stiffener tube during manufacture of the dilator.

FIG. 4 is an illustrative view of stiffener tube 32 and sleeve 34 during manufacturing of dilator 14. In the illustrated embodiment, stiffener tube 32 has a substantially uniform cross-section. Sleeve 34 also has a substantially uniform cross-section. The inside diameter of the sleeve 34 is approximately the same as the outside diameter of the stiffener tube 32. In this manner, the sleeve 34 can be positioned over and along the length of the stiffener tube 32. As is illustrated in FIG. 4, the length of sleeve 34 is somewhat longer than the length of stiffener tube 32. The additional length of sleeve 34 allows the tip of sleeve 34 to extend beyond the stiffener tip 38. By positioning sleeve 34 over the stiffener tube 32, sleeve 34 does not directly contact the surface of stiffener tip 38.

Because sleeve 34 does not directly contact the front surface of stiffener tip 38, the transition from stiffener tube 32 to the tip of sleeve 34 results in a potential point of buckling or kinking of sleeve 34. This is largely due to the fact that the greater rigidity of the stiffener tube 32 and the somewhat more flexible and resilient nature of the sleeve 34 changes the overall characteristics of dilator 14 at the interface corresponding with stiffener tip 38. In the event that lateral forces are exerted on the tip of sleeve 34,. the portion of sleeve 34 which is positioned distally to stiffener tip 38 can undergo some deformation without resulting in buckling of the sleeve 34. However, due to the increased strength and rigidity provided to dilator 14 by stiffener tube 32, the resilience of sleeve 34 begins to be substantially limited at stiffener tip 38. The natural resilient deformation of the portion of sleeve 34 positioned distally to stiffener tip 38 can result in buckling at the portion of the sleeve corresponding with stiffener tip 38. As a result, instead of providing increased strength at the sleeve tip, stiffener tip 38 becomes a point of weakness in the dilator which can result in failure of the tip of the sleeve. As will be appreciated by those skilled in the art, FIG. 4 represents a step in the manufacturing process and does not correspond with the final configuration of the dilator or any resulting design implications of the components shown in FIG. 4.

Figure 5:
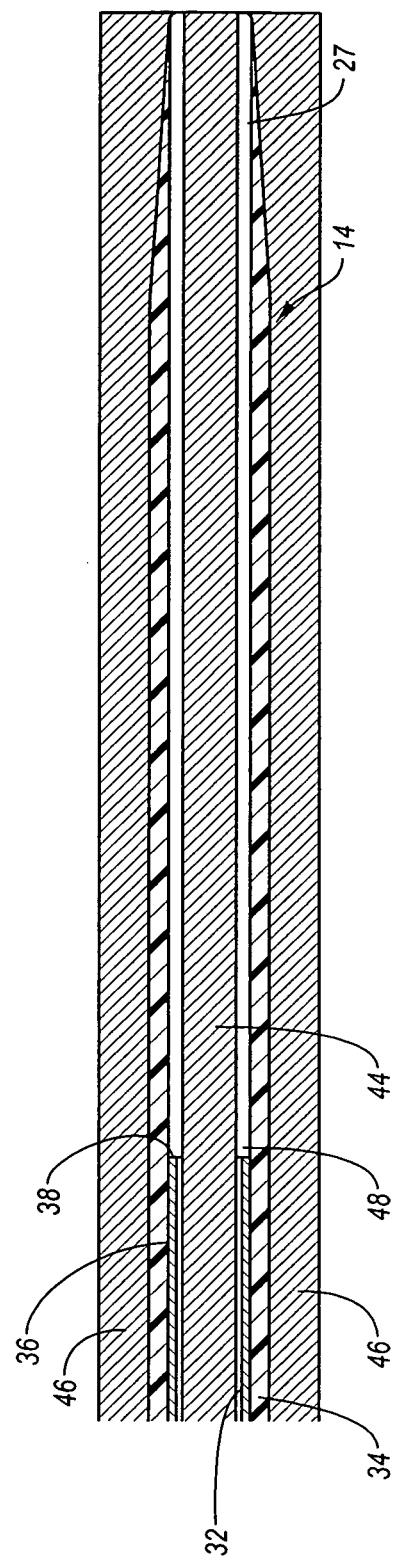
FIG. 5 is a perspective view of the mandrel and die assembly for use with the stiffener tube and sheath prior to flow back of the sheath during manufacture of the dilator.

FIG. 5 is a perspective view of stiffener tube 32 and sleeve 34 subsequent to positioning of a mandrel 44 and die 46 during manufacture of dilator 14. In the illustrated embodiment, a mandrel 44 has been inserted along the length of stiffener tube 32 terminating at the distal end of sleeve 34. Similarly, die 46 has been inserted along the outside diameter of sleeve 34 terminating at a point corresponding with the distal end of sleeve 34. In the illustrated embodiment, mandrel 44 has an outside diameter which corresponds with the inside diameter of stiffener tube 32. Die 46 has an inside diameter which substantially corresponds with the outside diameter of sleeve 34. However, die 46 has a somewhat tapered configuration at the portion of sleeve 34 positioned distally to stiffener tip 38. The tapered configuration of die 46 allows for the creation of a taper in the tip of dilator 14 that facilitates the insertion of dilator 14 into the patient.

The tapered configuration of die 46 results in contact of sleeve 34 with the distal portion of mandrel 44. However, due to the configuration of stiffener tip 38 and the positioning of sleeve 34 along the length of stiffener tube 32, an air gap 48 is created adjacent the portion of mandrel 44 positioned directly distal to stiffener tip 38. As previously discussed, air gap 48 can result in weakness at the stiffener tube/sleeve interface 36 due to the fact that sleeve 34 does not contact the front surface of stiffener tip 38. Once mandrel 44 and die 46 have been positioned along the length of stiffener tube 32 and sleeve 34, heat is conveyed from mandrel 44 and die 46 to form sleeve 34 to stiffener tube 32. The heat conveyed by die 46 and mandrel 44 to the portion of sleeve 34 which is positioned distally to stiffener tip 38 also results in deformation of sleeve 34. The deformation of the sleeve 34 continues until the material of the tip of sleeve 34 begins to flow back into the air gap area 48 adjacent stiffener tip 38. This allows for the material from which sleeve 34 is formed to fill the air gap 48 and provide for a dilator tip having greater strength.

As will be appreciated by those skilled in the art, a variety of types and configurations of mechanisms for forming stiffener tube to the sleeve can be utilized without departing from scope and spirit of the present invention. Additionally, a variety of types and configurations of methods and apparatus can be utilized to create flow back or increased material properties in the area of the stiffener tip without departing from the scope and spirit of the present invention. For example, in one embodiment, radio frequency heat is provided from the mandrel and die to form the sleeve to the stiffener tube. In another embodiment, other thermal properties, mechanical forming, or chemical processes are utilized to form the sleeve to the stiffener tube. In yet another embodiment, forming of the sleeve to stiffener tube is provided in the absence of a mandrel and die configuration. In yet another embodiment, instead of providing flow back of the material from which the sleeve is formed to fill the air gap, a secondary member is formed to the sleeve in a manner that the tip of the dilator contacts the stiffener tip to provide for increased strength at the stiffener tip. In another embodiment, while a contact surface of the catheter tip is provided, an air gap is positioned between the contact surface and the stiffener tip. When forces are exerted on the catheter tip, flexing of the sheath results in closing of the air gap and interaction between the contact surface of the catheter tip and the stiffener tip in a manner that provides increased strength at the transition.

Figure 6:
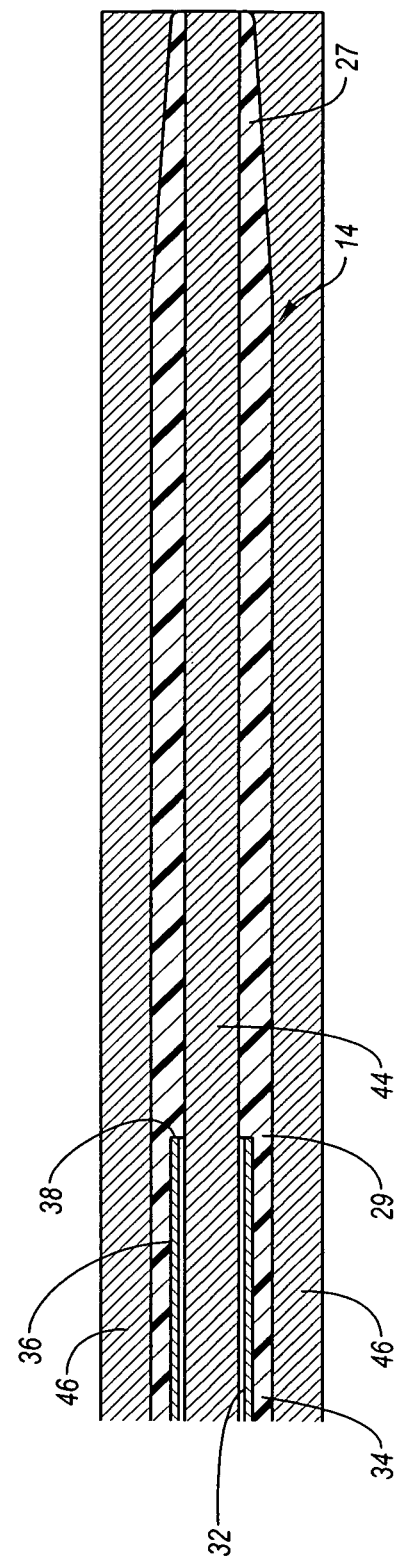
FIG. 6 is a perspective view of the mandrel and die assembly subsequent to flow back of the sheath of the dilator tip during manufacture of the dilator.

FIG. 6 is a cutaway cross-sectional view of the dilator 14 subsequent to heating of sleeve 34 to form sleeve 34 to stiffener tube 32. Additionally, FIG. 6 illustrates the portion of sleeve 34 positioned distally to the stiffener tip 38 subsequent to flowback of the material of sleeve 34 into air gap 48 (see FIG. 5.) In the illustrated embodiment, the shape of dilator tip 27 is formed subsequent to flowback of the material from which sleeve 34 is formed.

The flowback of the sleeve material results in a configuration of dilator tip 27 in which a contact surface is provided between dilator tip 27 and the front surface of stiffener tip 38. By providing a contact surface between dilator tip 27 and the front surface of stiffener tip 38, greater stability and strength is provided subsequent to forces being exerted on the distal end of dilator tip 27. As a result, when forces are exerted on dilator tip 27, the forces are conveyed directly from dilator tip 27 to the stiffener tube 32. This minimizes excessive lateral movement that can result from forces which are exerted in a perpendicular vector relative to the front of dilator tip 27. Additionally, stiffener tube 32 can provide additional support and strength to dilator tip 27 facilitating proper insertion of dilator tip 27 into the patient. The combination of the contact surface for interaction with stiffener tip 38 and the strain-relief properties provided by interaction of the catheter sheath and the dilator tip 27, provides a catheter tip 27 having increased strength while also providing resistance to kinking or failure of the catheter tip 27 at transition 29.

Subsequent to flowback of the material from which sleeve 34 is comprised and the formation of dilator tip 27, die 46 and mandrel 44 are withdrawn from dilator 14. Dilator 14 can then be inserted into a catheter sheath, as illustrated in FIG. 3. Once the dilator 14 is inserted into the catheter sheath 12, as illustrated in FIG. 3, the introducer sheath assembly 10 is ready to be inserted into the patient.

The flowback of the materials from which sleeve 34 is comprised and the configuration of dilator tip 27 provide for a substantially uniform inside diameter along the length of the dilator 14. By providing a substantially uniform inside diameter, guidewires, other materials, or implements can be introduced and withdrawn along the length of dilator 14 without obstruction. In the illustrated embodiment, the inside diameter of dilator 14 substantially corresponds with both the inside diameter of the stiffener tube 32 and the outside diameter of the mandrel 44.

By utilizing a mandrel and die configuration in connection with a stiffener tube and sleeve, flow back of sleeve 34 can be effectuated to provide a contact surface of the dilator tip for interaction with the front surface of the stiffener tip. The dilator can be manufactured in a quick and efficient manner without requiring specialized machinery, components, materials, or properties other than the mandrel and die configuration as depicted in reference to FIGS. 5 and 6. As a result, the system and method of manufacturing the dilator is both straightforward and cost-effective. As a result, a catheter tip is provided having increased strength which can be manufactured in a cost effective manner.

As will be appreciated by those skilled in the art, a variety of types and configurations of dilatore and systems and methods of manufacturing dilatore can be provided without departing from the scope and spirit of the present invention. For example, in one embodiment, additional steps or processes are provided to create additional coatings or tapers of the dilator. In another embodiment, a die having a substantially conical configuration is provided to create the taper of the dilator tip. In another embodiment, flowback of the material from which the sleeve is formed occurs in a step that is separate from forming of the sleeve to the stiffener tube. In yet another embodiment, the material from which the sleeve is formed is separate from the material which is utilized to form all or part of the catheter tip.

What is claimed is:

1. A dilator for use with an introducer sheath assembly, the introducer sheath assembly being configured for insertion into a vasculature or body cavity of a patient, the dilator configured to be inserted through a lumen of the introducer sheath assembly to provide rigidity to the introducer sheath assembly for insertion of the introducer sheath assembly into the patient, the dilator comprising:

a dilator hub disposed at a proximal end of the dilator and including a coupler configured for mating engagement with an introducer sheath hub coupled to a proximal end of a catheter sheath of the introducer sheath assembly;

a dilator tip positioned at a distal end of the dilator, the dilator tip having a proximal portion and a distal portion, the proximal portion of the dilator tip being configured to be positioned inside the catheter sheath of the introducer sheath assembly such that a length of the proximal portion of the dilator tip is positioned proximal to a distal tip of the catheter sheath, and the distal portion of the dilator tip configured to be positioned outside the catheter sheath and distal to the distal tip of the catheter sheath, wherein the dilator tip defines a contact surface in a plane that intersects the longitudinal axis of a stiffener tube and the contact surface is configured to be positioned within the catheter sheath when the dilator is inserted into the catheter sheath and the dilator hub is coupled to the introducer sheath hub, the dilator tip further defining a taper adjacent a distal end of the dilator tip wherein the contact surface is spaced proximally of the taper; and a stiffener tube coupled to the dilator hub and extending from the dilator hub to the contact surface of the dilator tip, the stiffener tube defining a front surface in a plane that intersects the longitudinal axis of the stiffener tube, wherein the front surface is disposed parallel to and in abutment with the contact surface of the dilator tip to form a transition between the stiffener tube and the dilator tip, wherein the transition is configured to be positioned proximal to a distal tip of the catheter sheath, within the catheter sheath, when the dilator hub is coupled to the introducer sheath, wherein the dilator tip is configured to be withdrawn proximally from the introducer sheath assembly during a procedure in which the introducer sheath assembly is inserted into the patient, wherein the dilator hub is configured such that coupling the dilator hub to the introducer sheath hub is configured to position the proximal portion of the dilator tip within the distal tip of the catheter sheath.

2. The dilator of claim 1, wherein the transition is provided at the distal end of the stiffener tube and the proximal portion of the dilator tip.

3. The dilator of claim 2, wherein the transition is configured to be positioned inside the catheter sheath when the dilator is inserted into the introducer sheath assembly from the proximal end.

4. The dilator of claim 1, wherein the contact surface is formed from flow back of the material from which the dilator tip is formed during manufacture.

5. The introducer sheath assembly of claim 1, wherein the dilator tip comprises a sleeve extending proximally from the contact surface and configured to be disposed around and external to the stiffener tube.

6. The introducer sheath assembly of claim 5, wherein the sleeve extends along a full length of the stiffener tube.

7. An introducer sheath assembly configured for insertion into a vasculature or body cavity of a patient, the introducer sheath assembly comprising:
 a catheter sheath comprising a tubular member having a lumen defined therethrough and configured to be inserted into a patient;
 an introducer sheath hub disposed at a proximal end of the catheter sheath and configured to enable engagement with the catheter sheath;
 a dilator positionable internal to, and along a length of the lumen of the catheter sheath, the dilator comprising:
  a dilator hub disposed at a proximal end of the dilator and including a coupler configured to engage the introducer sheath hub;
  a stiffener tube having a proximal end connected to the dilator hub and a distal end defining a front surface in a plane that intersects a longitudinal axis of the stiffener tube, wherein the distal end is configured to be positioned proximally to a distal tip of the catheter sheath, within the catheter sheath, when the dilator hub is coupled to the introducer sheath hub; and
  a sleeve positioned external to the stiffener tube, a distal end of the sleeve extending beyond the distal end of the stiffener tube and defining a dilator tip, the dilator tip having a proximal portion and a distal portion, the proximal portion of the dilator tip being configured to be positioned inside the catheter sheath when the dilator hub is coupled to the introducer sheath hub, the proximal portion of the dilator tip defining a contact surface in a plane that intersects the longitudinal axis of the stiffener tube, wherein the contact surface is disposed parallel to and in abutment with the front surface of the stiffener tube to form a transition between the stiffener tube and the dilator tip, the distal portion of the dilator tip configured to be positioned outside the catheter sheath when the dilator hub is coupled to the introducer sheath hub, the dilator tip further defining a taper adjacent a distal end of the dilator tip wherein the contact surface is spaced proximally of the taper,
 wherein the sleeve, including the dilator tip, and the stiffener tube are configured to be advanced into the catheter sheath concurrently in a distal direction and are configured to be withdrawn proximally from the catheter sheath during a procedure in which the introducer sheath assembly is inserted into a patient,
 wherein the transition between the stiffener tube and the tip of the dilator, including the front surface and the contact surface, is configured to be positioned proximal to a distal tip of the catheter sheath, within the catheter sheath, when the dilator hub is coupled to the introducer sheath hub, and
 wherein the catheter sheath is configured to provide strain relief to the dilator tip at a point distal to the distal end of the stiffener tube in response to lateral movement of the dilator tip to prevent lateral kinking of the dilator tip at the transition between the stiffener tube and the tip of the dilator.

8. The introducer sheath assembly of claim 7, wherein the dilator tip has a thicker wall than a wall of the sleeve that is positioned external to the stiffener tube.

9. The introducer sheath assembly of claim 8, wherein the wall of the dilator tip is formed by deformation of the portion of the sleeve extending beyond the distal end of the stiffener tube.

10. The introducer sheath assembly of claim 7, wherein the sleeve is positioned around and external to the stiffener tube along a full length of the stiffener tube.

11. The introducer sheath assembly of claim 7, wherein the contact surface is formed from flow back of the material from which the sleeve, including the dilator tip, is formed during manufacture.

12. An introducer sheath assembly comprising:
 a catheter sheath that extends between a proximal end and a distal end; and
 a dilator that is configured to be inserted into the catheter sheath, the dilator comprising:
  a dilator hub disposed at a proximal end of the dilator and including a coupler to allow for engagement with an introducer sheath hub coupled to a proximal end of the catheter sheath;
  a stiffener tube having a proximal end coupled to the dilator hub and a distal end defining a front surface in a plane that intersects a longitudinal axis of the stiffener tube, wherein the distal end is configured to be positioned proximal to a distal tip of the catheter sheath, within the catheter sheath, when the dilator hub is coupled to the introducer sheath hub; and
  a sleeve positioned externally to the stiffener tube and being more flexible than the stiffener tube, the sleeve defining a dilator tip having a contact surface in a plane that intersects the longitudinal axis of the stiffener tube, wherein the contact surface is disposed parallel to and in abutment with the front surface of the stiffener tube to form a transition between the stiffener tube and the dilator tip, wherein the dilator tip extends distally beyond the distal end of the stiffener tube such that, when the dilator is inserted into the catheter sheath, the dilator tip further defining a taper adjacent a distal end of the dilator tip wherein the contact surface is spaced proximally of the taper:
   the distal end of the stiffener tube is within the catheter sheath and is distanced from the distal end of the catheter sheath;
   a first portion of the dilator tip that extends distally beyond the distal end of the stiffener tube is also within the catheter sheath such that the catheter sheath provides strain relief at and distal to the transition between the stiffener tube and the dilator tip to limit lateral kinking of the dilator tip at a transition between the stiffener tube and the dilator tip; and a second portion of the dilator tip that extends distally beyond the distal end of the stiffener tube also extends distally beyond the distal end of the catheter sheath, wherein the stiffener tube and the sleeve are fixed relative to a proximal end of the dilator such that both the stiffener tube and the sleeve are configured to be introduced and advanced into the catheter sheath through the proximal end of the catheter sheath and are configured to be withdrawn proximally from the catheter sheath during a procedure in which the introducer sheath assembly is inserted into a patient.

13. The introducer sheath assembly of claim 12, wherein the sleeve includes an outer coating to the stiffener tube so as to facilitate sliding of the dilator along a full length of the catheter sheath during insertion of the dilator into the catheter sheath.

14. The introducer sheath assembly of claim 12, wherein the portion of the sleeve that extends proximally from the dilator tip defines a substantially uniform cross-section that is larger than a substantially uniform cross-section defined by the stiffener tube.

15. The introducer sheath assembly of claim 12, wherein the sleeve is positioned over the stiffener tube along a full length of the stiffener tube.

16. The introducer sheath assembly of claim 12, wherein the stiffener tube and the sleeve are fixed relative to the dilator hub.

* * * * *